US007096718B2

(12) United States Patent
Matzner et al.

(10) Patent No.: US 7,096,718 B2
(45) Date of Patent: Aug. 29, 2006

(54) PRESSURE TESTING APPARATUS

(75) Inventors: Mark D. Matzner, Burleson, TX (US);
J. Allen Sutton, Weatherford, TX (US)

(73) Assignee: S.P.M. Flow Control, Inc., Fort Worth, TX (US)

( * ) Notice: Subject to any disclaimer, the term of this patent is extended or adjusted under 35 U.S.C. 154(b) by 169 days.

(21) Appl. No.: 10/755,456

(22) Filed: Jan. 12, 2004

(65) Prior Publication Data
US 2005/0150272 A1    Jul. 14, 2005

(51) Int. Cl.
*G01M 3/02* (2006.01)
(52) U.S. Cl. ............................................. 73/37
(58) Field of Classification Search ............... 73/37, 73/40, 41, 45, 45.1–45.4; 86/50
See application file for complete search history.

(56) References Cited

U.S. PATENT DOCUMENTS 3,465,572 A * 9/1969 Covert ..................... 73/49.2

2003/0209133 A1* 11/2003 Greenfield et al. ............ 86/50
2004/0107823 A1* 6/2004 Kiley et al. .................... 86/50

* cited by examiner

*Primary Examiner*—Charles Garber
(74) *Attorney, Agent, or Firm*—Bracewell & Giuliani LLP

(57) ABSTRACT

A portable test compartment allows for on-site pressure testing of a workpiece at the site where the workpiece is utilized, instead of having to haul the workpiece to an off-site testing location. A test vehicle carries the elongated test compartment, and travels to the on-site location to test the workpiece. The vehicle has a lift assembly that pivotally connects the vehicle and the compartment. The lift assembly moves the compartment from a storage position alongside the vehicle to an operational position alongside the ground. The compartment has an interior portion that receives the workpiece. Inside the compartment, a safety blanket is fastened to the bottom of the compartment. The safety blanket envelops the workpiece by folding several portions of the blanket around the workpiece.

9 Claims, 5 Drawing Sheets

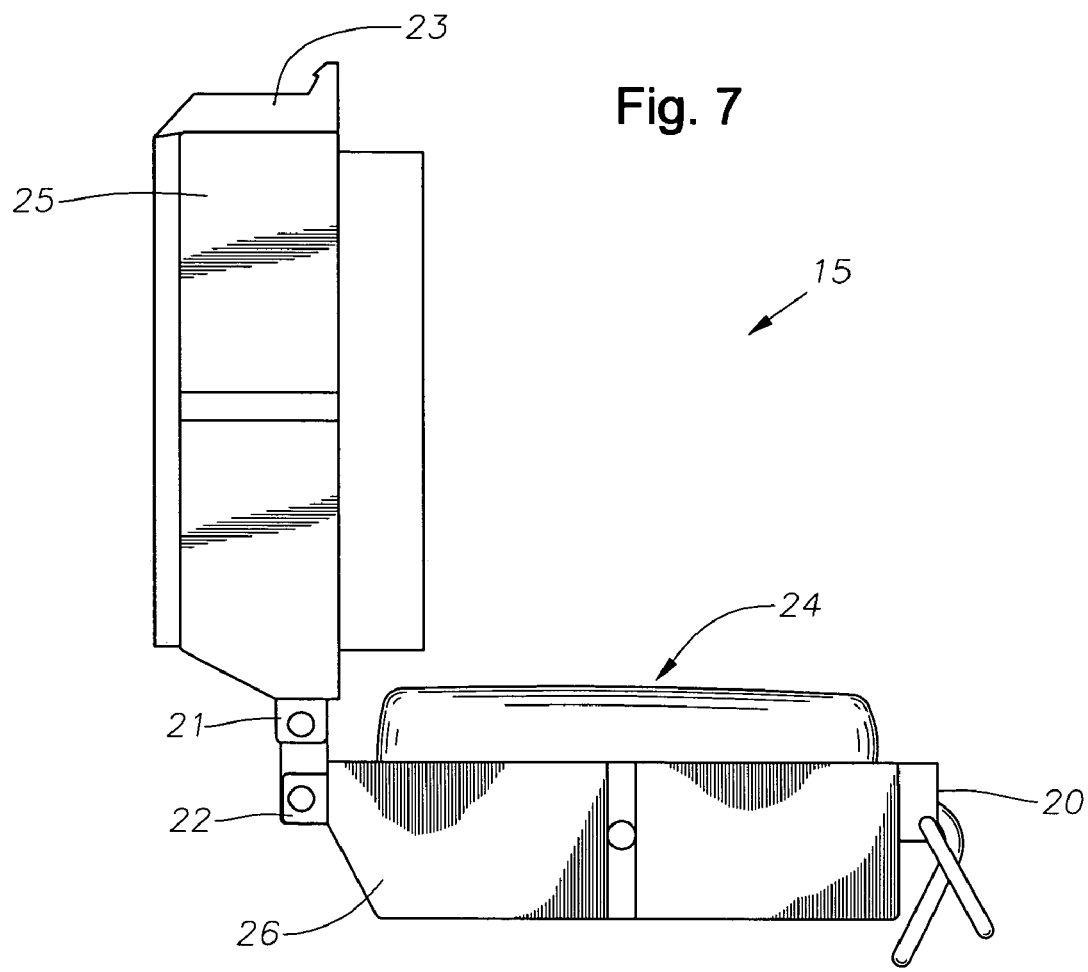
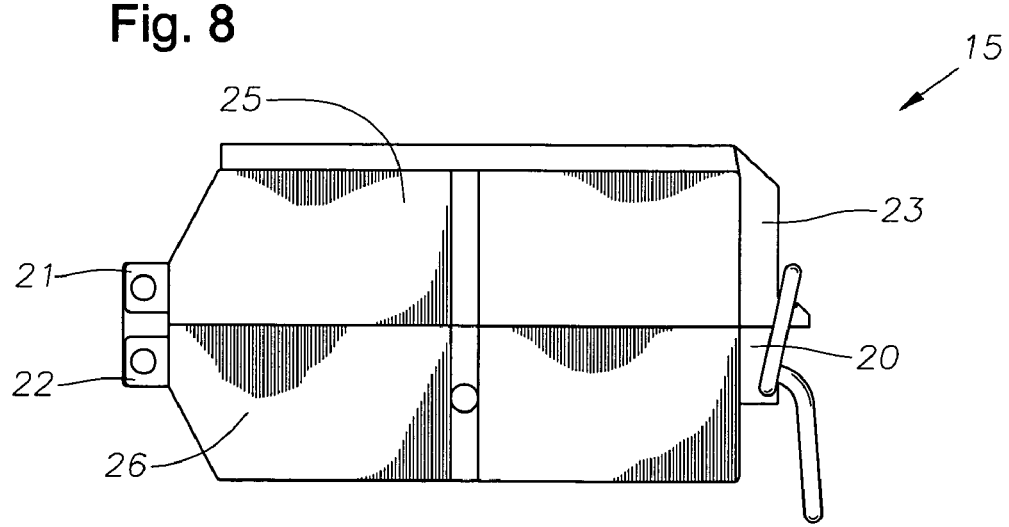

PRESSURE TESTING APPARATUS

1. FIELD OF THE INVENTION

The present invention relates generally to pressure testing a workpiece. It relates more particularly to pressure testing a workpiece in a test compartment carried by a vehicle, whereby the vehicle travels to an on-site location to pressure test the workpiece.

2. BACKGROUND OF THE INVENTION

The present invention relates to test flowline equipment in the context of oil field pumping, where it is necessary to pump with high pressure in the range of 10,000-15,000 psi. The high pressure pumping is used in such instances as pumping cement or viscous chemicals from a well through a flowline.

In the course of operating the flowline equipment, the flowline workpiece must periodically undergo testing. A common method of testing is to carry the flowline workpiece away from the oil field to an off-site location to perform the proper testing. It is inconvenient and costly to carry the equipment off-site for testing each time such testing was necessary. As such, a need in the art exists for a device that enables testing flowline equipment directly on-site at the oil field.

Furthermore, an additional challenge to on-site testing is the safety risks associated with pumping at 10,000–15,000 psi. Such safety accommodations were readily available at off-site testing centers. However, the safety accommodations from the off-site locations have proven difficult to move to the on-site location because of size, weight, and other practical considerations. Therefore, any solution to the aforementioned problem must combine on-site convenience with the necessary pressure testing safety.

3. SUMMARY

The present invention allows for on-site pressure testing of a workpiece at the site where the workpiece is utilized, instead of having to haul the workpiece to an off-site testing location. A test vehicle carries an elongated test compartment, and travels to the on-site location to test the workpiece. The vehicle has a lift assembly that pivotally connects the vehicle and the compartment. The lift assembly moves the compartment from a storage position alongside the vehicle to an operational position alongside the ground. The compartment has an interior portion that receives the workpiece. Inside the compartment, a safety blanket is fastened to the bottom of the compartment. The safety blanket envelops the workpiece by folding several portions of the blanket around the workpiece.

The novel features of this invention, as well as the invention itself, will best be understood from the following drawings and detailed description.

4. BRIEF DESCRIPTION OF THE DRAWINGS

FIG. 7 is an end view of the test compartment of FIG. 4, shown in the open position.

FIG. 8 is an end view of the test compartment of FIG. 4, shown in a closed position.

5. DETAILED DESCRIPTION OF THE INVENTION

Although the following detailed description contains many specific details for purposes of illustration, anyone of ordinary skill in the art will appreciate that many vairations and alterations to the following details are within the scope of the invention. Accordingly, the exemplary embodiment of the invention described below is set forth without any loss of generality to, and without imposing limitations thereon, the claimed invention.

Figure 1:
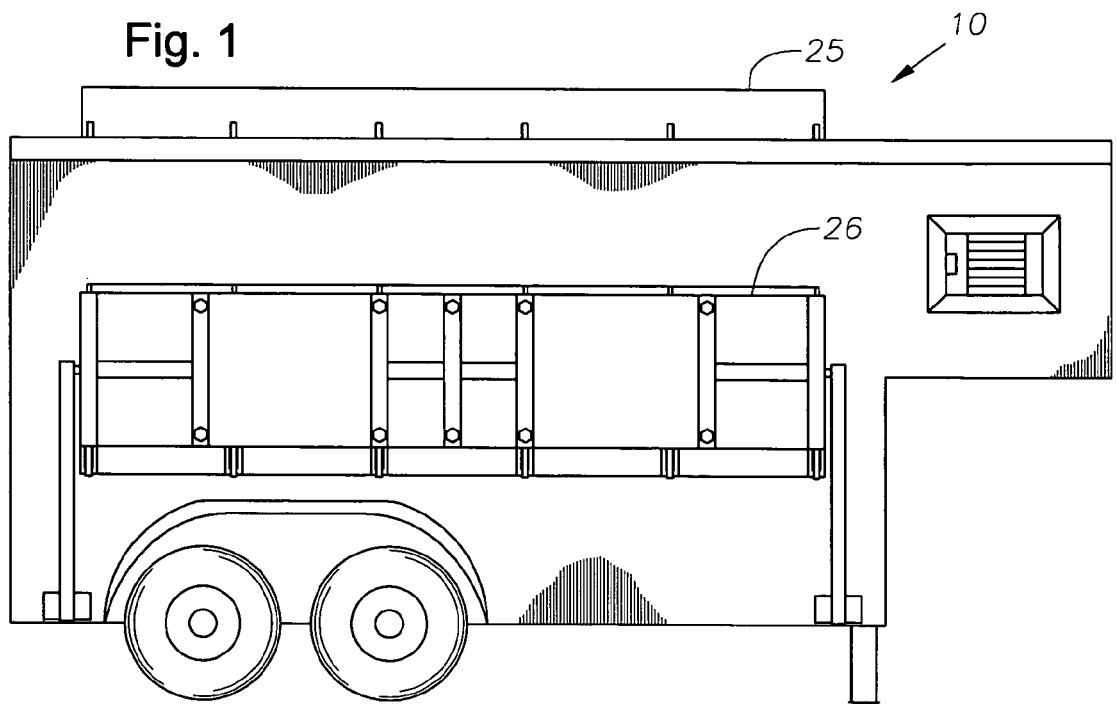
FIG. 1 and FIG. 2 show a front view and side view, respectively, of a test vehicle carrying a test compartment.
Figure 2:
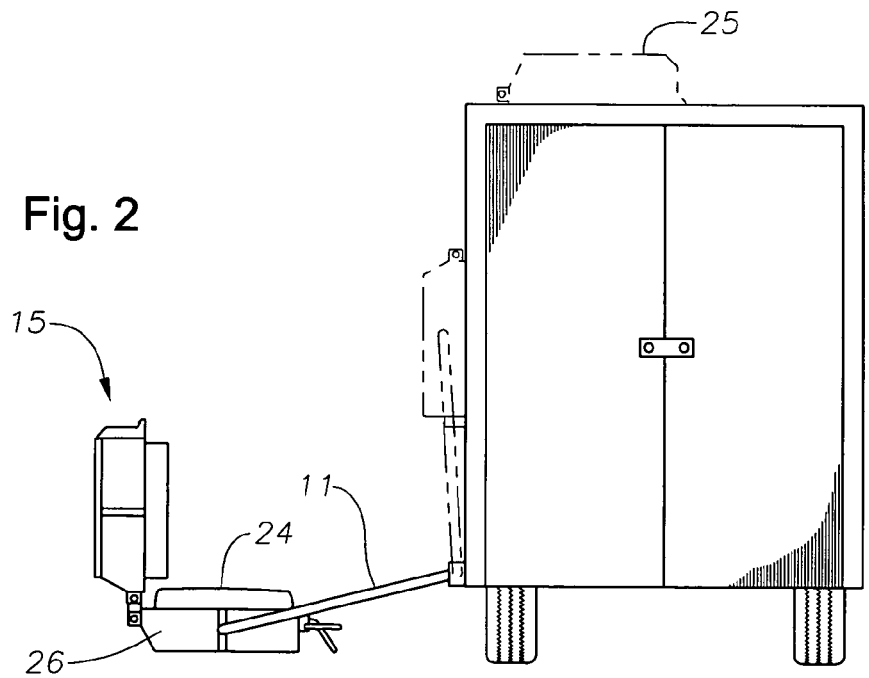

FIG. 1 and FIG. 2 show a front view and side view, respectively, of test vehicle 10 carrying test compartment 15. Test vehicle 10 carries testing equipment to an on-site location for pressure testing of a workpiece such as an oil field flowline, flowline union, swivel, check and relief valve, and the like. Test vehicle 10 carries an elongated test compartment 15 comprising tray 26 and lid 25. In this exemplary embodiment, tray 26 is carried in a vertical plane on the side of test vehicle 10, and lid 25 is detached from tray 26 and carried on the roof of test vehicle 10. Lift assembly 11 comprises at least one arm that pivotally connects the side of test vehicle 10 and the tray 26.

To position the apparatus for testing, lift assembly 11 lowers tray 26 from alongside test vehicle 10 in a storage position toward the ground to an operational position. As shown by the drawings, lift assembly 11 tilts test compartment 15 from a vertical plane in the storage position to a horizontal plane in the operational position. Lid 25 is removed from the roof of test vehicle 10 by a crane or the like, and hingeably connected to tray 26. Tray 26 and lid 25 as attached together are collectively referred to as test compartment 15. After testing all of the workpieces, lid 25 is disconnected from tray 26 and placed once again on the roof, and lift assembly 11 raises tray 26 to its initial storage position alongside test vehicle 10.

Figure 3:
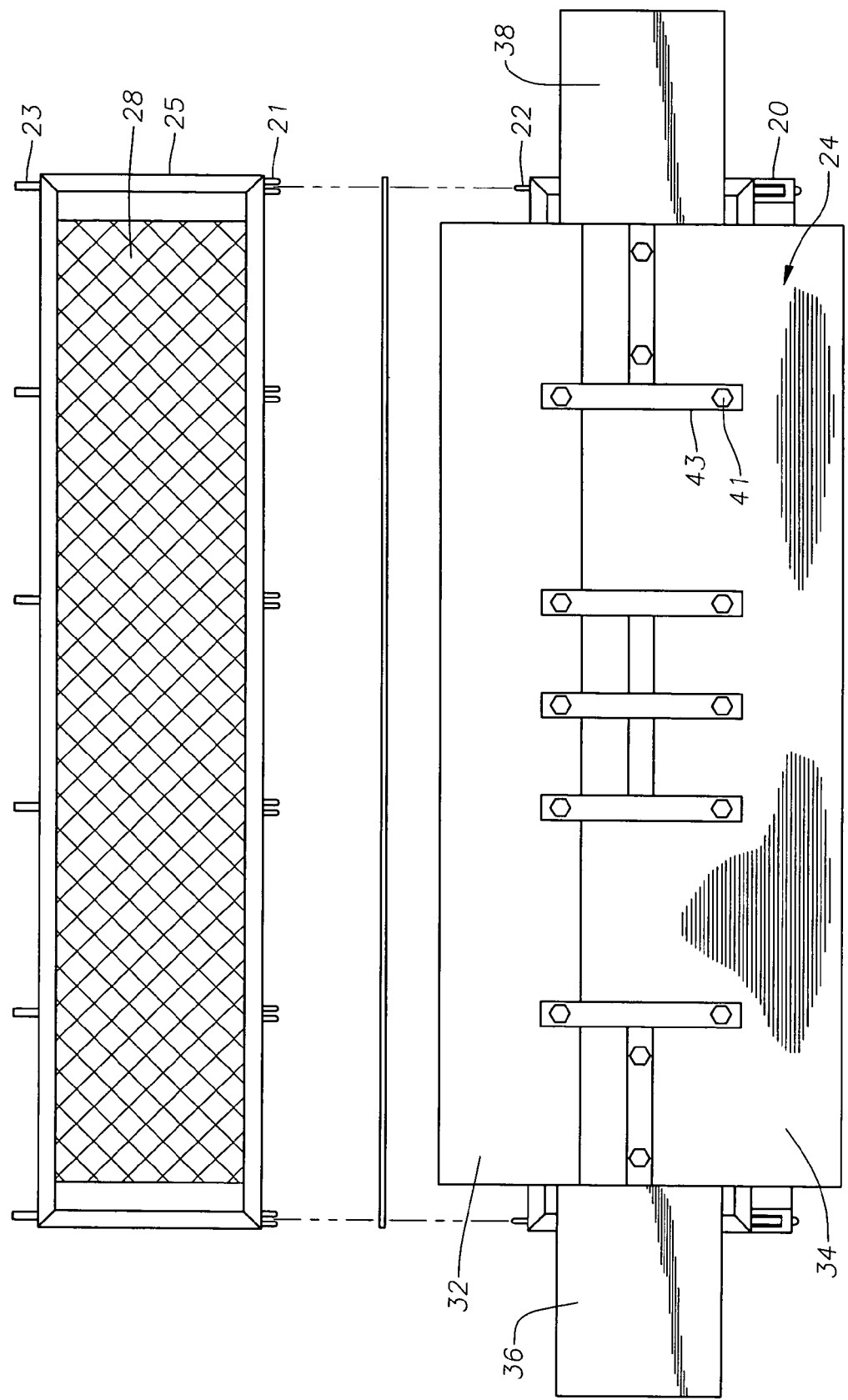
FIG. 3 depicts a top view of a tray of a test compartment supporting a safety blanket shown a folded-out position, and a lid shown in exploded form from the tray.

FIG. 3 depicts a top view of tray 26 of test compartment 15, with lid 25 detached from tray 26 in exploded form from tray 26. As further demonstrated by FIG. 7 and FIG. 8, tray 26 has a bottom, two side walls, two end walls, fasteners to receive bolts 41, and a drain hole (not shown) for draining the pressure testing fluid after pressure testing operations are completed. When lid 25 is attached to tray 26, lid 25 is substantially parallel and co-planar with the bottom portion of tray 26. Tray 26 is made from steel, and lid 25 is made from steel with a perforated top comprising apertures.

Figure 6:
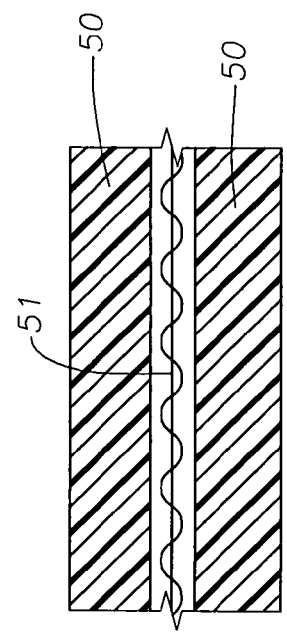
FIG. 6 is a cross sectional view of the safety blanket of FIG. 5, taken along the line 6—6 of FIG. 5.

In FIG. 3, safety blanket 24 is shown assembled within tray 26 in a folded-out position. In the exemplary embodiment, safety blanket 24 is assembled from four separate blankets bolted together inside tray 26, including two larger elongated blankets 32, 34 and two smaller end blankets 36, 38. The blankets are designed to be thick enough to withstand the intense pressure testing inside test compartment 15. As shown in FIG. 6, safety blanket 24 comprises an inside layer 51 of material such as kevlar in between two outside layers 50 of material such as vinyl.

Figure 4:
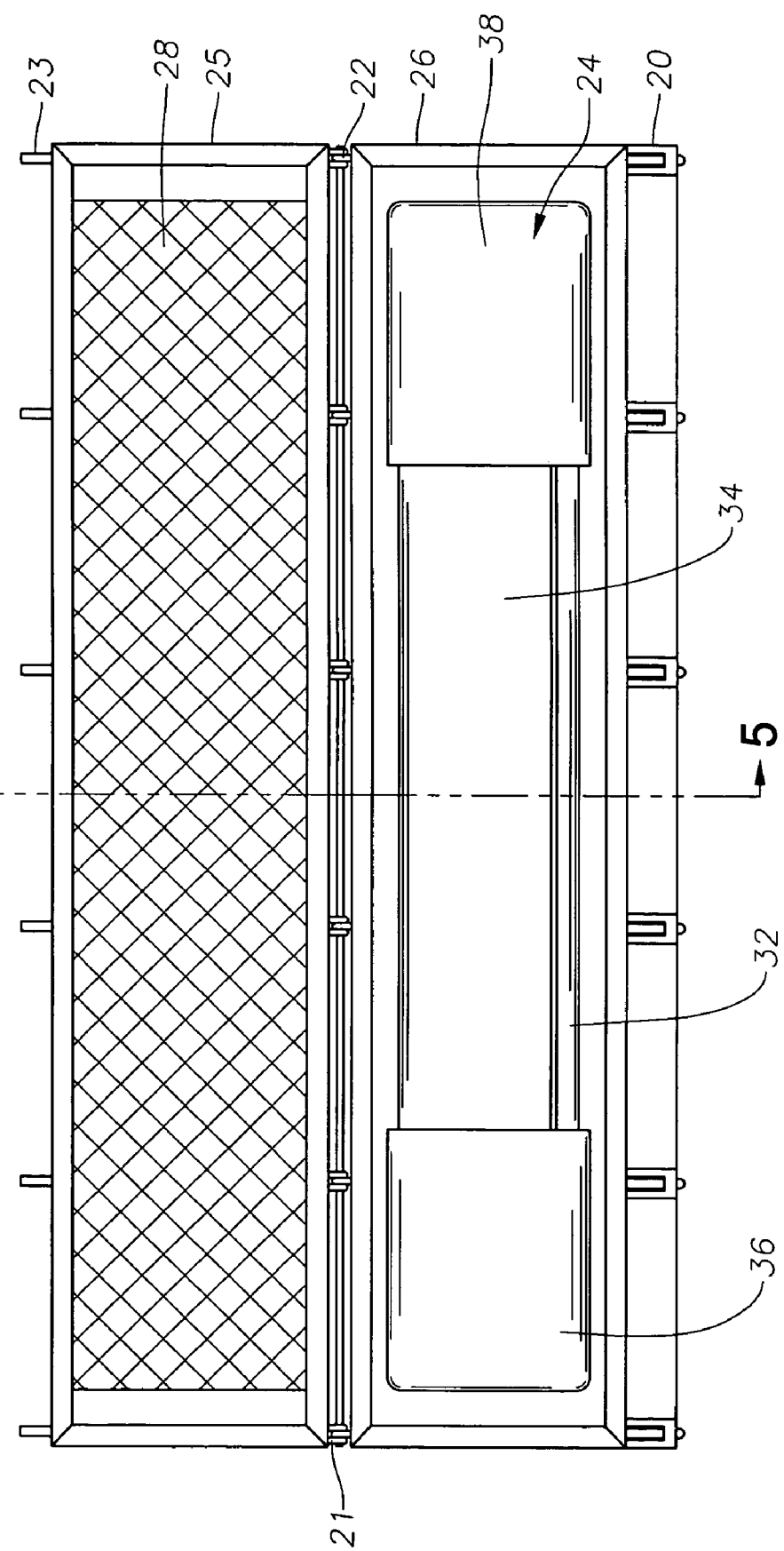
FIG. 4 depicts a top view of a tray of the test compartment of FIG. 3, showing the safety blanket in a folded-in position around a workpiece.

Safety blanket 24 is folded around workpiece 40 as shown in FIG. 4. First, one of the larger elongated blankets 32 folds over workpiece 40. Second, the other larger elongated blanket 34 folds over and substantially overlaps the first blanket. Finally, each smaller end blanket 36, 38 is folded over the overlapping elongated blankets. After all blankets overlap each other, no further metal strips 43 are necessary to complete the folding sequence.

Referring to the exemplary embodiment of FIG. 3, safety blanket 24 is fastened to tray 26 by bolts 41 housed in metal strips 43 located throughout the length of the elongated tray 26. Bolts 41 and metal strips 43 must be strong enough to withstand the intense pressure occurring during testing of workpiece 40, so that safety blanket 24 does not detach from tray 26. Safety blanket 24 folds over workpiece 40 at several positions alongside tray 26, most notably just outside where bolts 41 are located.

In FIG. 4, and further demonstrated by FIG. 7 and FIG. 8, lid 25 hingeably attaches to tray 26 on one elongated side, and latchably attaches to tray 26 on the other elongated side, collectively forming test compartment 15. Tray hinge 22 aligns and connects with lid hinge 21, while tray latch 20 aligns and connects with lid latch 23. Lid 25 has a frame that includes apertures 28 on its top side.

FIG. 7 and FIG. 8 depict a side view of test compartment 15 comprising a tray 26 and lid 25, wherein test compartment 15 is shown in the open and closed position, and whereby workpiece 40 is wrapped in safety blanket 24 within the test compartment 15. In this exemplary embodiment, lid hinge 21 is aligned and connected with tray hinge 22 both in the open position and in the closed position. The hinge connecting tray 26 and lid 25 includes a releasable pin, which when removed, enables one to remove lid 25 from tray 26 for storage. On the other side of the elongated test compartment 15, lid latch 23 is aligned and connected to tray latch 20 only in the closed position when pressure testing is about to commence.

Figure 5:
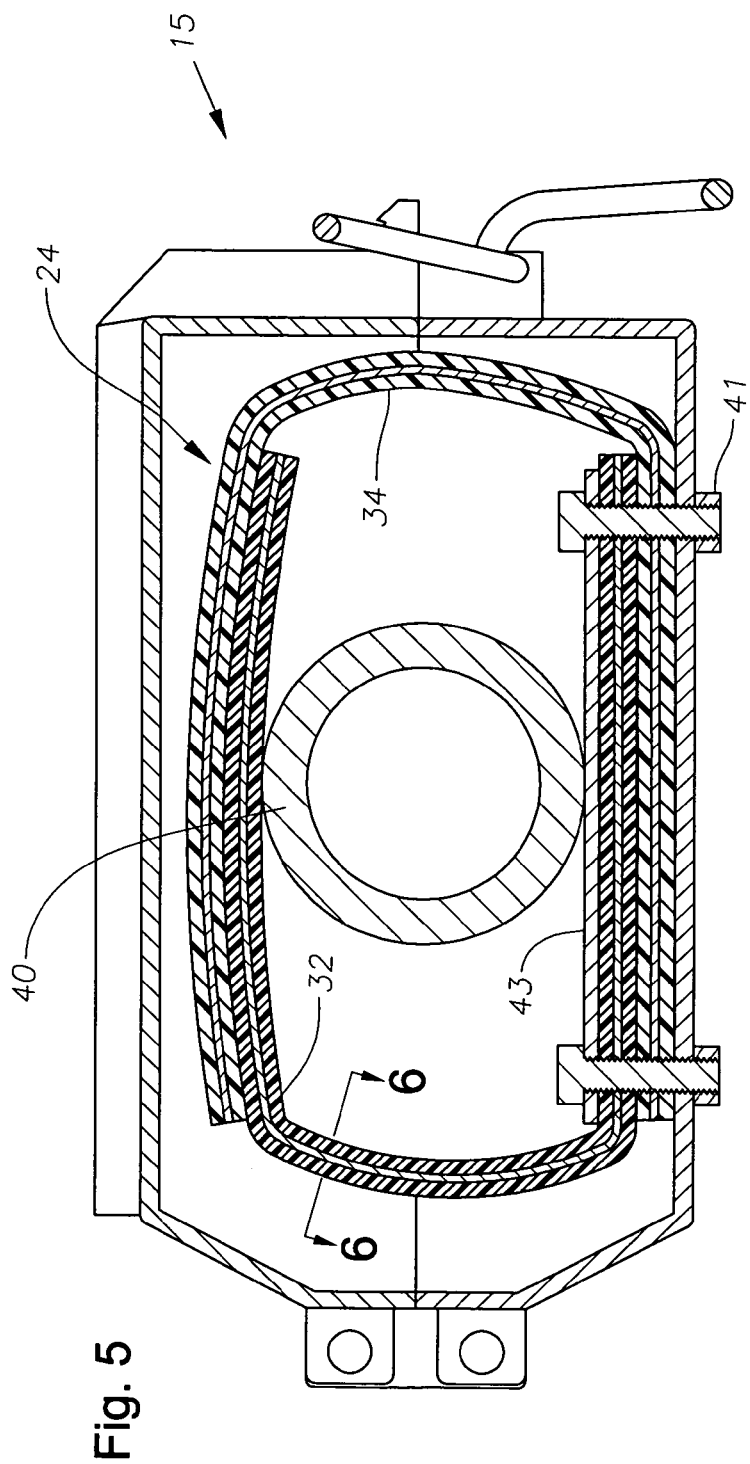
FIG. 5 is a cross sectional view of the test compartment of FIG. 4, taken along the line 5—5 of FIG. 4.

FIG. 5 depicts a cross sectional side view of a closed test compartment 15, within which workpiece 40 and safety blanket 24 are encased. Safety blanket 24 is shown folded around workpiece 40. As shown in the embodiment, safety blanket 24 is folded several times at several different angles around workpiece 40. First, one of the larger elongated blankets 32 folds over workpiece 40. Second, the other larger elongated blanket 34 folds over and substantially overlaps the first blanket. Finally, each smaller end blanket 36, 38 is folded over the overlapping elongated blankets. Bolts 41 housed in metal strips 43 secure safety blanket 24 to tray 26 of test compartment 15, enabling workpiece 40 to remain generally stationary during pressure testing operations.

FIG. 6 shows a cross sectional view of safety blanket 24. In this exemplary embodiment, safety blanket 24 comprises multiple layers of material. The outside layers 50 comprises an elastomeric material, and the inside layer 51 comprises a woven layer of aramid fiber. While these materials are utilized in this particular embodiment, the materials used for the outside layer 50 and inside layer 51 can vary according to the circumstances of the testing situation. For example, in another embodiment, outside layer 50 comprises rubber, vinyl, or plastic, while inside layer 51 comprises a kevlar material.

In operation, test vehicle 10 carries test compartment 15 comprising tray 26 and lid 25 to an on-site location for pressure testing of workpiece 40. To position the apparatus for testing, lift assembly 11 lowers tray 26 from alongside test vehicle 10 in a storage position toward the ground to an operational position. As shown by the drawings, lift assembly 11 tilts test compartment 15 from a vertical plane in the storage position to a horizontal plane in the operational position. Lid 25 is removed from the roof of test vehicle 10 and hingeably connected to tray 26.

Upon directing test compartment 15 to the operational position, safety blanket 24 is arranged in the folded-out position, and workpiece 40 is placed on safety blanket 24. Safety blanket 24 is folded around workpiece 40 as follows: First, one of the larger elongated blankets 32 folds over workpiece 40. Second, the other larger elongated blanket 34 folds over and substantially overlaps the first blanket. Finally, each smaller end blanket 36, 38 is folded over the overlapping elongated blankets. To close test compartment 15 before testing, lid 25 closes about the hinges 21, 22, and a testing operator latches lid 25 to tray 26 at latches 20, 23 to secure lid 25 in a juxtaposed position against tray 26.

After closing and latching test compartment 15 with safety blanket 24 and workpiece 40 encased within test compartment 15, testing operations may commence. After testing all of the workpieces, the hinge connecting lid 25 and tray 26 is disconnected, and lid 25 is placed once again on the roof. Finally, lift assembly 11 raises tray 26 to its initial storage position alongside test vehicle 10.

Although the present invention and its advantages have been described in detail, it should be understood that various changes, substitutions, and alterations can be made hereupon without departing from the principle and scope of the invention. Accordingly, the scope of the present invention should be determined by the following claims and their appropriate legal equivalents.

That which is claimed is:

1. A method for pressure testing a workpiece, comprising:
   (a) placing a workpiece within an open tray of a testing compartment and folding an explosion resistant blanket around the workpiece; then
   (b) closing a lid of the compartment over the workpiece and the blanket; and
   (c) applying test fluid pressure to the workpiece.

2. The method of claim 1, wherein: step (a) further comprises fastening a portion of the blanket to the tray of the compartment, then placing the workpiece on said portion of the blanket, then folding another portion of the blanket over the workpiece.

3. The method of claim 1, wherein: step (a) comprises folding side portions of the blanket over sides of the workpiece and folding end portions of the blanket over ends of the workpiece.

4. The method according to claim 1, wherein step (a) comprises:
   placing a base portion of the blanket on a bottom of the tray of the compartment; then
   placing the workpiece on the base portion of the blanket; then
   folding a flap portion of the blanket over the workpiece.

5. The method according to claim 1, wherein step (a) comprises:
   providing the blanket with two pieces, each piece having a base portion and a flap portion;
   overlying and securing the base portions of the pieces to a bottom of the tray of the compartment; then
   placing the workpiece on the base portions of the blanket; then
   folding each of the flap portions over the workpiece, with one of the flap portions overlying the other.

6. The method according to claim 5, further comprising:
   providing the blanket with two end pieces, each of the end pieces having a bottom portion and a flap portion;

securing the bottom portions of the end pieces to the bottom of the tray of the compartment at opposite ends of the base pieces; then folding the flap portions of the end pieces over ends of the workpiece.

7. The method according to claim 1, wherein step (c) comprises:

applying liquid under pressure to the workpiece; and wherein the method further comprises:

relieving the pressure and draining the liquid within the compartment from a drain hole of the compartment.

8. A method for on-site pressure testing of a workpiece, the method comprising:

(a) mounting a test compartment to a lift assembly carried by a test vehicle;

(b) moving the compartment with the lift assembly from a storage position alongside the vehicle to an operational position extended from the vehicle toward the ground;

(c) wrapping the workpiece in a safety blanket;

(d) placing the workpiece within the compartment;

(e) applying test fluid pressure to the interior of the workpiece.

9. The method of claim 8, wherein: step (a) further comprises fastening a base portion of the blanket to the compartment, and wrapping the workpiece with a flap portion of the blanket.

* * * * *